Jan. 2, 1973 H. C. SWIM ET AL Plant Pat. 3,282
ROSE PLANT
Filed July 22, 1971
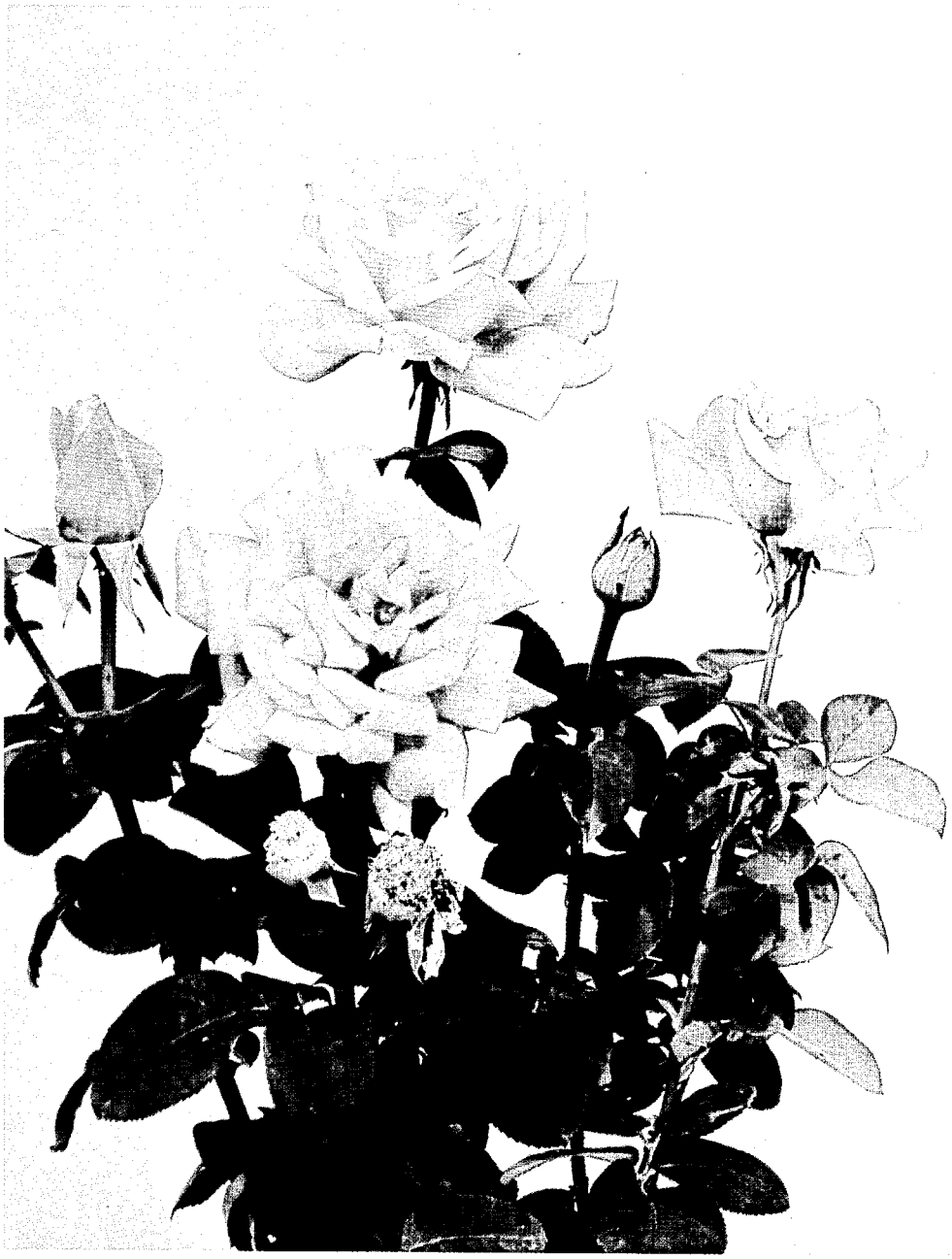
Inventors.
H. C. Swim
O. L. Weeks
By: Robb & Robb
Attorneys.

United States Patent Office

Plant Pat. 3,282
Patented Jan. 2, 1973

3,282

ROSE PLANT

Herbert C. Swim and O. L. Weeks, Ontario, Calif., assignors to The Conard-Pyle Company, West Grove, Pa.

Filed July 22, 1971, Ser. No. 165,412
Int. Cl. A01h *5/00*
U.S. Cl. Plt.—19 1 Claim

The present invention relates to a new and distinct variety of rose plant of the hybrid tea class, which was originated by us by crossing the rose variety known as "Peace" (Plant Patent No. 591) with an unnamed and unpatented seedling derived from crossing the rose variety known as "El Capitan" (Plant Patent No. 1,796) with an unnamed and unpatented seedling of "Happiness" (Plant Patent No. 911) X "Chrysler Imperial" (Plant Patent No. 1,167). In the final cross, the variety "Peace" was the seed parent and the unnamed seedling was the pollen parent.

As the result of this breeding, we have produced a new and improved rose variety which is distinguished from its antecedents, as well as from all other rose varieties of which we are aware, as evidenced by the following unique combination of characteristics which are outstanding in the new variety:

(1) Excellence of its hybrid tea habit;

(2) Particularly good foliage having above average disease resistance;

(3) A habit of bearing most of the flowers singly and on long and strong stems;

(4) An ability to retain a high centered flower bud conformation through substantially the entire flower life;

(5) A distinctive, attractive and outstanding pink flower color which is maintained throughout the blooming stages from bud to open flower;

(6) An unusually strong, pleasant and true rose flower fragrance; and (7) Good lasting flower qualities and remontance of bloom which give the overall effect of almost continuous blooms on an attractive plant which is well covered with excellent foliage.

In comparison with its pollen parent, our new variety has better foliage substance and the foliage is larger in size and lighter green in color; it has a normal complement of thorns as distinguished from the very few thorns of this parent; the flowers have more petals and are borne almost always singly, with only occasional clusters, contrary to this parent; and the flower color is pink instead of bright red like the flower color of this parent.

As compared with its seed parent "Peace," the foliage of our new variety is not quite as leathery, and is larger in size and brighter green in color; the flower buds are longer, more pointed and better shaped, but the open flowers are not as large or as fully petaled as the open flowers of this parent which have from 10 to 20 more petals per flower; the pink color of the flower buds and open flowers is completely different from the flower color of "Peace" which is basically yellow; and the flowers have a very strong rose fragrance while the flowers of "Peace" have no fragrance.

Asexual reproduction of our new rose variety by budding, as performed at Chino, Calif., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make this same in a color illustration of this character.

The following is a detailed description of our new variety, with color terminology in accordance with the Nickerson Color Fan, published by Munsell Color Company Incorporated, of Baltimore, Md., except where general color terms of ordinary dictionary significance are obvious:

Type: Hardy; tall; bush; outdoor; seedling; for cut flowers and for garden decoration.
Class: Hybrid tea.
Breeding: Seedling.
*Seed parent.*—"Peace."
*Pollen parent.*—An unnamed seedling.
Propagation: Holds its distinguishing characteristics through succeeding propagations by budding.

*Flowers*

Locality where grown and observed: In fields and greenhouses at Chino and Ontario, Calif.
Flowers borne: Mostly singly, but occasionally 2 or 3 to stem; on strong, long stems.
Quantity of bloom: From free to abundant, outdoors.
Continuity: From intermittent to continuous.
Fragrance: Very strong. Nature—True rose perfume.
Bud:
*Peduncle.*—Very short; heavy caliper; erect; smooth; few, if any, hairs. Color—From light to medium green.
*Before calyx breaks.*—Size—large. Form—medium length; pointed; ovoid; with foliaceous appendages on the surface of the bud; with bristle-like foliaceous parts extending beyond the tip of the bud equal to ¼ or more of its length.
*As calyx breaks.*—Color—Strong Purplish Red, Hue 7.5 RP 5/12.
*As petals first open.*—Size—large. Form—pointed; ovoid. Color—outside—between Strong Purplish Red, Hue 7.5 RP 4/11 and Strong Purplish Red, Hue 10 RP 4/12, with very small area at base Brilliant Yellow Green, Hue 2.5 GY 9/8. Inside—considerably brighter than Strong Purplish Red, Hue 10 RP 4/12, with small area at base Brilliant Green Yellow, Hue 7.5 Y 9/8.
*Opening.*—Opens up well; is not retarded or prevented from opening or destroyed by cold, hot, wet or dry weather.
Bloom:
*Size (when fully open).*—Large; from 4 inches to 6 inches.
*Petalage.*—Double, but stamens not hidden; from 26 to 35 petals, plus some petaloids which are usually quite small; arranged regularly.
*Form.*—High-centered at first and remaining high-centered; petals at first being tightly rolled outward, but later becoming loosely rolled outward at maturity.
Petals:
*Texture.*—Fairly thick and leathery.
*Appearance.*—Inside—satiny. Outside—satiny.
*Shape.*—Outside—Broadly round, with apex flat and usually with 1 notch. Intermediate—broadly round and scalloped, with apex flat and entire. Inside—broadly round and irregularly scalloped, with apex flat and entire.

This description of a newly opened flower was made from a rose grown outdoors during the month of October at Ontario, Calif.

Color:
*Outer petal.*—Outside surface—between Deep Purplish Pink, Hue 7.5 RP 6/12 and Strong Purplish Red, Hue 7.5 RP 5/12, with a minute segment at base of petal Brilliant Yellow Green, Hue 2.5 GY 9/8. Inside surface—considerably brighter than Strong Purplish Red, Hue 7.5 RP 5/12, with a small basal segment Brilliant Yellow Green, Hue 2.5 GY 9/8.

*Intermediate petal.*—Outside surface—Deep Purplish Pink, Hue 7.5 RP 6/12, with a small basal segment Brilliant Yellow Green, Hue 7.5 Y 9/8. Inside surface—Strong Purplish Red, Hue 7.5 RP 5/12, with a minute basel segment Brilliant Greenish Yellow, Hue 10 Y 9/9.

*Inner petal.*—Outside surface—Strong Purplish Red, Hue 7.5 RP 5/12, with a minute basal segment Brilliant Greenish Yellow, Hue 7.5 Y 9/8. Inside surface—considerably brighter than Strong Purplish Red, Hue 7.5 RP 4/11, with a minute basal segment Brilliant Greenish Yellow, Hue 7.5 Y 9/8.

This description was made from a rose that was open for three days outdoors during the month of October at Ontario, Calif.

Color:

*Outer petal.* — Outside surface — between Strong Purplish Red, Hue 7.5 RP 5/12 and Strong Purplish Pink, Hue 7.5 RP 6/12, with a minute basal segment Brilliant Yellow Green, Hue 2.5 GY 9/8. Inside surface—between Strong Purplish Red, Hue 7.5 RP 5/12 and Strong Purplish Pink, Hue 7.5 RP 6/12, with a minute basal segment Brilliant Greenish Yellow, Hue 2.5 GY 9/8.

*Inner petal.*—Outside surface—Deep Purplish Pink, Hue 7.5 RP 6/12, with a minute basal segment Brilliant Greenish Yellow, Hue 10 Y 9/9. Inside surface—considerably brighter than Deep Purplish Pink, Hue 7.5 RP 6/12, with a small basal segment Brilliant Greenish Yellow, Hue 10 Y 9/9.

General color effect:

*Newly opened flower.*—From Strong Purplish Red, Hue 7.5 RP 4/11 to Strong Purplish Red, Hue 7.5 RP 5/12, blending into Deep Purplish Pink, Hue 7.5 RP 6/12. 3-days open—from Strong Purplish Red, Hue 7.5 RP 5/12 to Deep Purplish Pink, Hue 7.5 RP 6/12, blending to Strong Purplish Pink, Hue 7.5 RP 7/10.

*Behavior.*—Drop off cleanly.

*Flower longevity.*—On bush in garden—from 3 to 5 days in October. Cut roses grown outdoors and kept at living room temperatures—from 3 to 5 days in October.

*Reproductive organs*

Stamens: Many; arranged irregularly about pistils; tucked in calyx.

Filaments: Medium length; many with anthers. Color—some yellow-reddishness.

Anthers: Medium size; open at various times. Color—some yellow-reddishness.

Pollen: Moderate quantity. Color—from gold to yellow.

Pistils: Many.

Styles: Uneven; from medium length to long; medium caliper; bunched.

Stigma: Color—from yellow to reddish.

Ovaries: All protruding from calyx.

Hips: None observed.

Sepals: Permanent; moderate length; spear-shaped; curled.

Color—from light to medium green.

Seeds: None observed.

*Plant*

Foliage:

*Leaves.*—Compound of 3 to 5 leaflets; very abundant; very large; heavy; leathery; glossy.

*Leaflets.* — Shape — ovate. Apex — from obtuse to acute. Base—from round to obtuse. Margin—simply serrate.

*Color.—Mature*—upper surfaces—Dark Green. Under surface—moderaely normal green. *Young*—upper surface—from moderately normal green to bronze. Under surface—moderately light red.

*Rachis (the supporting stem of the compound leaf).* — Heavy. Upper side — smooth; slightly grooved. Under side—moderately prickly.

*Stipules.*—Medium length; moderately wide; with points of medium length turning out at an angle or more than 45°.

*Disease resistance.*—Above average resistance to mildew and also resistant to blackspot, as determined by comparison with other rose varieties grown under comparable conditions at Chino and Ontario, Calif.

Growth:

*Habit.*—Bushy; upright; much-branched.

*Growth.*—Free and vigorous.

*Canes.*—Heavy caliper.

*Main stems.*—Color—dull green. *Large prickles*—few; short; hooked slightly downward; with short, narrow base. Color—Brown. *Small prickles*—several. Color—Brown. *Hairs*—none.

*Branches.*—Color—dull green. *Large prickles*—Several; from short to medium length; hooked downward; with short, narrow base. Color—Brown. *Small prickles*—from none to few. *Hairs*—none.

*New shoots.*—Color—dull green. *Large prickles*—several; medium length; hooked downward; with fairly long, narrow base. Color—very light brown, with a green intone. *Small prickles*—from none to few. *Hairs*—from none to few.

We claim:

1. A new and distinct variety of rose plant of the hybrid tea class, substantially as herein shown and described, characterized particularly as to novelty by the unique combination of excellence of its hybrid tea habit, particularly good foliage having above average disease resistance, a habit of bearing most of the flowers singly and on long and strong stems, an ability to retain a high-centered flower bud conformation through substantially the entire flower life, a distinctive, attractive and outstanding pink flower color which is maintained throughout the blooming stages from bud to open flower, an unusually strong, pleasant and true rose flower fragrance, and good lasting flower qualities and remontance of bloom which give the overall effect of almost continuous blooms on an attractive plant which is well covered with excellent foliage.

No references cited.

ROBERT E. BAGWILL, Primary Examiner.